(12) United States Patent
Mordon et al.

(10) Patent No.: US 10,561,856 B2
(45) Date of Patent: Feb. 18, 2020

(54) LIGHT EMITTING SYSTEM

(71) Applicants: INSERM (INSTITUT NATIONAL DE LA SANTE ET DE LA RECHERCHE MEDICALE), Paris (FR); UNIVERSITE DE LILLE 2 DROIT ET SANTE, Lille (FR); CENTRE HOSPITALIER REGIONAL ET UNIVERSITAIRE DE LILLE (CHRU), Lille (FR)

(72) Inventors: Serge Mordon, Loos (FR); Nacim Betrouni, Loos (FR); Laurent Mortier, Loos (FR)

(73) Assignees: INSERM (Institut National de la Santé et de la Recherche Médicale), Paris (FR); Université de Lille 2 Droit et Santé, Lille (FR); Centre Hospitalier Regional et Universitaire de Lille (CHRU), Lille (FR)

( * ) Notice: Subject to any disclaimer, the term of this patent is extended or adjusted under 35 U.S.C. 154(b) by 809 days.

(21) Appl. No.: 15/025,623

(22) PCT Filed: Nov. 25, 2014

(86) PCT No.: PCT/EP2014/075473
§ 371 (c)(1),
(2) Date: Mar. 29, 2016

(87) PCT Pub. No.: WO2015/078837
PCT Pub. Date: Jun. 4, 2015

(65) Prior Publication Data
US 2016/0220840 A1 Aug. 4, 2016

(30) Foreign Application Priority Data

Nov. 26, 2013 (EP) .................................... 13306621

(51) Int. Cl.
*A61N 5/06* (2006.01)

(52) U.S. Cl.
CPC ........ *A61N 5/062* (2013.01); *A61N 2005/063* (2013.01); *A61N 2005/0645* (2013.01); *A61N 2005/0659* (2013.01)

(58) Field of Classification Search
CPC .............................. A61N 5/06; A61N 2005/06
See application file for complete search history.

(56) References Cited

U.S. PATENT DOCUMENTS

| 2002/0138120 A1* | 9/2002 | Whitehurst | A61N 5/062 607/88 |
| 2006/0206173 A1* | 9/2006 | Gertner | A61N 5/0616 607/88 |

(Continued)

FOREIGN PATENT DOCUMENTS

| EP | 0 812 573 A2 | 12/1997 |
| WO | 2007/106856 A2 | 9/2007 |
| WO | 2013/092505 A1 | 6/2013 |

*Primary Examiner* — Lynsey C Eiseman
(74) *Attorney, Agent, or Firm* — W&C IP

(57) ABSTRACT

The system comprises: —a bundle of light fibers (11) connected to a light-emitting source (8), and both transmitting light inside the light fiber and emitting light toward a treatment volume (V), —a temperature-modifying system attached to the bundle of light fibers (11) to modify temperature in the treatment volume (V).

10 Claims, 6 Drawing Sheets

(56) References Cited

U.S. PATENT DOCUMENTS

| | | | | |
|---|---|---|---|---|
| 2007/0055329 A1* | 3/2007 | Hicks | ............ | A61F 7/02 |
| | | | | 607/112 |
| 2007/0208395 A1* | 9/2007 | Leclerc | ............ | A61N 5/0616 |
| | | | | 607/86 |
| 2009/0018622 A1* | 1/2009 | Asvadi | ............ | A61N 5/0621 |
| | | | | 607/91 |

* cited by examiner

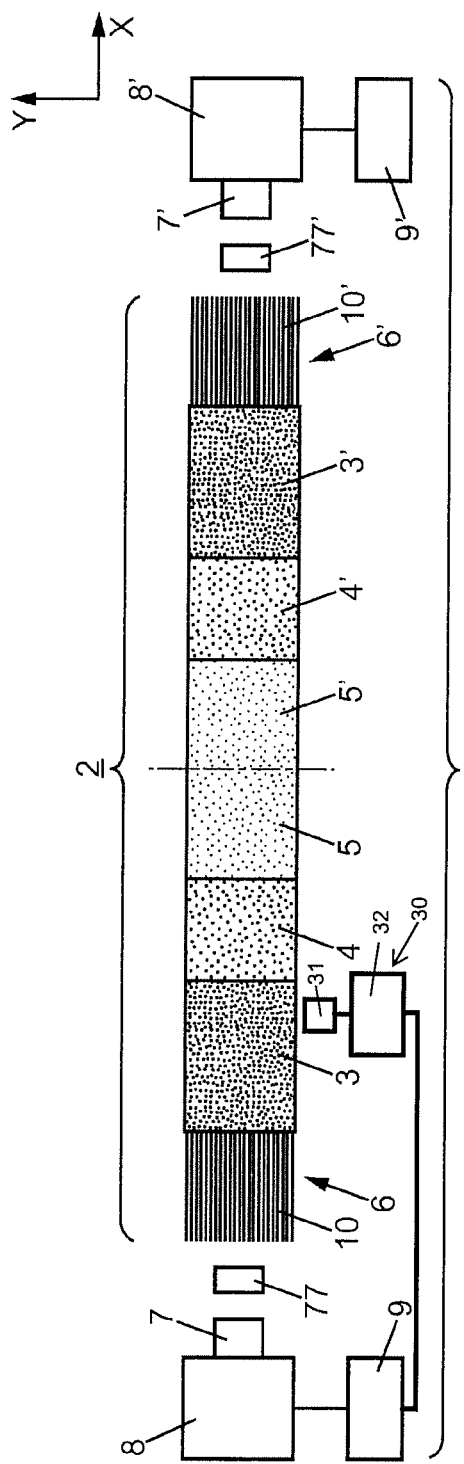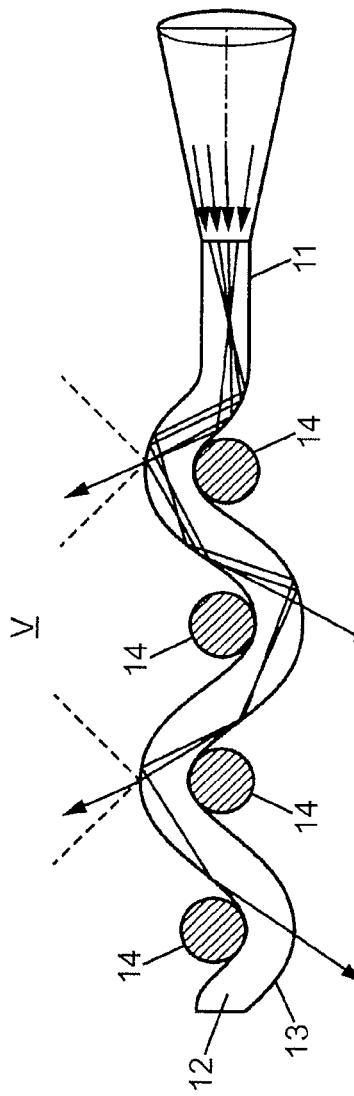
FIG. 1
FIG. 2

LIGHT EMITTING SYSTEM

FIELD OF THE INVENTION

The instant invention relates to light-emitting systems.

BACKGROUND OF THE INVENTION

In particular, the instant invention is related to light-emitting systems used for photo-dynamic therapy.

Photodynamic therapy (PDT) is a non-thermal technique which can be used to produce localised tissue necrosis. This requires activating a photosensitizer with light of a specific wavelength to form a cytotoxic species from molecular oxygen (mostly singlet oxygen). For a photodynamic reaction to occur, the photosensitizer, activating light and oxygen must be present in sufficient amounts.

The photosensitizer could be synthesized endogenously under the influence of a pre-administered precursor. The formation of the cytotoxic species requires the pre-administration of a species, which, below, is generally called the "drug".

The therapeutic effect of photodynamic therapy depends on a combination of parameters that include drug dose, drug-light interval, oxygen and light fluence rate. It also varies according to the wavelength distribution of the light source. Finally, a homogeneous and reproducible fluence rate delivery during clinical PDT is determinant in preventing under- or overtreatment. In dermatology, topical PDT has been carried out with a wide variety of light sources delivering a broad range of light doses. Irradiance is usually limited to less than 100 mW·cm$^{-2}$.

Light-emitting diodes (LEDs) are now considered as an appropriate light source for PDT. Indeed, LEDs have a relatively narrow bandwidth (usually 20 to 30 nm) and are available in a wide range of wavelengths. LED systems for Methyl aminolevulinate PDT (MAL-PDT) such as Aktilite® CL 16 and Aktilite® CL 128 (Metvix, Galderma) are now mainly used. The Aktilite® CL 16 treats areas of skin measuring 40×50 mm whereas the Aktilite® CL 128 treats larger areas (80×180 mm). They provide light doses of 37 J·cm$^{-2}$ required for the optimal activation of the associated photosensitizer. Fluence rate varies between 70 and 100 mW·cm$^{-2}$, for an irradiation time varying between 6 and 10 minutes. However even commercial systems, such as Aktilite® CL 16, do not deliver a uniform light distribution (Moseley, 2005). In the case of the CL 16, the irradiance may be as low as 38% of the central area at a distance of only 2 cm. These measurements were made on a flat surface. The heterogeneity is even greater during illumination of curved surfaces (face or scalp).

Thus, a homogeneous and reproducible fluence delivery rate during clinical photodynamic therapy plays a determinant role in preventing under- or over-treatment. Photodynamic therapy applied in dermatology has been carried out with a wide variety of light sources delivering a broad range of more or less adapted light doses. Due to the complexity of human anatomy, such as the human face and also vulval, and perianal areas, these light sources do not in fact deliver a uniform light distribution to the skin.

In dermatology, the clinical use of 5-aminolaevulinic acid (ALA) induced protoporphyrin IX (PPIX) for photodynamic therapy is proposed for non-melanoma skin cancer treatment. However, this treatment is painful, limiting the suitability of photodynamic therapy as a treatment of first choice. Patients report a burning or tingling sensation that sometimes leads to need for local anesthesia or termination of therapy. Especially treating extensive field cancerization with actinic keratosis in the face and scalp region is painful for the patient.

One way to reduce the pain consists in light dose fractionation. Irradiation is interrupted at a particular point for a period of time. There is therefore a succession of illumination periods and of rest periods. Besides, light fractionation also increases the efficiency: light fractionation produces more necrosis than with the same light dose delivered without rest periods.

Conventional light sources necessary for photodynamic therapy are expensive. Therefore an inactive or rest period is a waste of medical means.

Consequently the use of PDT has largely been limited to hospital outpatient services where costs can be high and the service inconvenient for the patient.

New concepts in illumination, such as ambulatory PDT or daylight illumination might contribute to the further acceptance of this method.

Additionally, actinic keratosis (AK) are scaly or crusty growths (lesions) caused by damage from the sun's ultraviolet rays (UVR). Actinic Keratosis is also known as solar keratosis. Untreated actinic keratosis can advance to squamous cell carcinoma (SCC), the second most common form of skin cancer. Treatment options include ablative (destructive) therapies such as cryosurgery, curettage with electrosurgery, and photodynamic therapy. Topical photodynamic therapy for actinic keratosis is now a well established treatment modality, with two drugs registered for this indication. In the last years, new formulations have been developed, which promise a further improvement of actinic keratosis treatment. Photodynamic therapy is well tolerated, has excellent cosmetic results, and has reported cure rates between 69 and 93%, with fewer side effects compared to the other treatment options. Presently, a flat LED panel is used as light source.

A conventional protocol using Metvix® (methyl aminolevulinate) consists in having Metvix® specifically absorbed into the altered skin cells of these lesions. Metvix® causes compounds called porphyrins to accumulate and be absorbed selectively by the actinic keratosis. Metvix® is applied to the lesions to be treated. The lesion is covered with a dressing. There is a 3 hour waiting period for the Metvix® cream to be absorbed and metabolized. After 3 hours, Metvix® is washed off and the patient is immediately illuminated with a red light, the intensity and time exposed to red light depends on the type of lesions that are treated. Light exposure can last between 8-20 minutes. The illumination is not homogeneous since a LED panel is used.

The size and the design of the led panel are not appropriate for bald scalps. Since the treatment is performed in a short period of time, the treatment is usually very painful.

One challenge in order to ensure the development of such treatment is to guarantee a uniform light illumination of the skin due to the complexity of the human anatomy.

Now the present inventors have developed a new medical device which allows delivering a uniform light distribution to complex body shapes and high fluence rate of illumination. Indeed, the development of flexible light sources considerably improves the homogeneity of light delivery. The integration of plastic optical fibres into textile structures offers an interesting alternative to rigid light emitters. It has also been shown that such light-emitting textiles do not heat at all, which enables their use for a long time by the patient.

However, one remaining factor which still limits the use of ambulatory PDT is the long time necessary to obtain sufficient amounts of the photosensitizer. One strives to reduce this time.

SUMMARY OF THE INVENTION

To this aim, it is provided a system comprising:
a bundle of light fibers, each light fiber comprising at least one connection end to be connected to a light-emitting source, and a longitudinal body adapted both to transmit light inside the light fiber along the longitudinal body and to emit light outside the longitudinal body along the longitudinal body toward a treatment volume,
a temperature-modifying system attached to the bundle of light fibers, and adapted to modify temperature in the treatment volume by at least 1° C., preferably by at least 5° C., more preferably by 10° C.

The invention provides an integrated system which can both emit light toward the treatment volume and modify temperature in the treatment volume, thereby enabling to perform a full photodynamic therapy procedure with a single device.

In some embodiments, one might also use one or more of the following features:
the bundle of light fibers is encompassed within a first layer, and the temperature-modifying system is provided as a second layer, superimposed with the first layer;
the bundle of light fibers comprises a light-emitting side and an opposite side, and the temperature-modifying system is provided on the opposite side of the bundle;
the temperature-modifying system comprises light fibers extending in parallel with the light fibers of the bundle and each having a connection end to a light-emitting source, the temperature-modifying system comprising a infra-red light-emitting source connected to said connection ends, and a control system adapted to have the infra-red light-emitting source emit infra-red light to modify temperature in the treatment volume;
the temperature-modifying system comprises a phase-change material adapted to change phase within a pre-set temperature range within 10° C. of body temperature;
the pre-set temperature range is between 37° C. and 45° C.;
the temperature-modifying system comprises yarns extending transverse to the light fibers, phase-change material being integral with said yarns;
said yarns and said fibres are woven together;
the temperature-modifying system comprises a infra-red light-emitting source connected to at least some connection ends, and a control system adapted to have the infra-red light-emitting source emit infra-red light to modify temperature in the treatment volume;
the bundle of light fibres has a concave shape adapted to wrap around a convex part of a human body;
the bundle of light fibres is flexible;
the system comprises a temperature-regulation system, the temperature-regulation system comprises a sensor attached to the bundle of light fibers, and adapted to detect temperature in the treatment volume, a controller adapted to receive temperature information from the sensor and to control the temperature-modifying system according to the temperature information;
the system further comprises a heater adapted to pre-heat the phase change material at a temperature within the pre-set temperature range;
the system further comprises a light-emitting source optically connected to the connection ends, and adapted to emit light into the light fibers;
the light-emitting source is settable to emit light at one or more pre-set wavelength range used in photodynamic therapy;
the system further comprises a sensor sensible to detect fluorescence light entering at least one of the light fibers from the treatment volume.

BRIEF DESCRIPTION OF THE DRAWINGS

Other characteristics and advantages of the invention will readily appear from the following description of one of its embodiments, provided as a non-limitative example, and of the accompanying drawings.

On the drawings:

FIG. 1 is a top view of a medical device according to a first embodiment,

FIG. 2 is a schematic detailed view of a woven optical fibre,

On the different Figures, the same reference signs designate like or similar elements.

DETAILED DESCRIPTION

Figure 3:
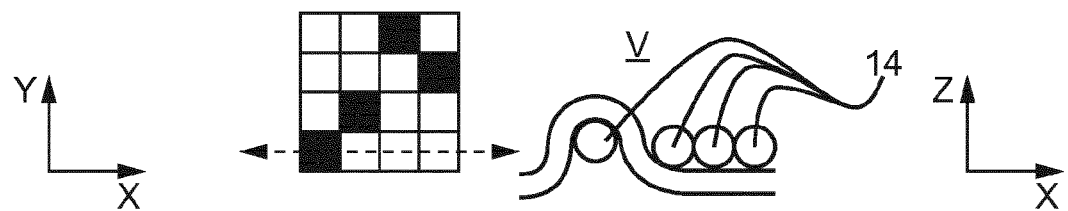
FIGS. 3, 4 and 5 include each a top view and a sectional view of patterns of satin weave 4, 6 and 8, respectively.

FIG. 1 schematizes a medical system 1 according to a first embodiment of the invention. The medical system 1 comprises a flexible light-diffusing textile 2. According to this embodiment, the flexible light-diffusing textile 2 can comprise three individual light diffuser textile portions 3, 4, 5. These textile portions are arranged one after the other along a longitudinal direction X. The flexible light-diffusing textile 2 is a thin textile sheet which can be laid flat in a plane X-Y, and is largely flexible out of that plane, in bending and/or torsion. The thickness of the textile sheet along the Z axis is little compared to the dimensions of the flexible light-diffusing textile in the other two directions. X-Y-Z form an orthogonal frame of reference. Further, in the present example, the flexible light-diffusing textile is made symmetrical with respect to the axis X. Therefore, in the present example, the flexible light-diffusing textile 2 further comprises textile portions 5', 4', 3', respectively similar to the textile portions 5, 4, 3, and arranged in that order from the textile portion 5 along the axis X. Textile portions 3, 4, 5, 5', 4', 3' form together the woven area of the flexible light-diffusing textile 2.

The flexible light-diffusing textile 2 comprises a bundle of light fibers extending sensibly in parallel to the direction X. Each light fiber comprises a longitudinal body having two opposite ends.

In order to connect the light diffusing textile 2 to a light-emitting source, a part of the length of the optical fibres is free. The free sections 6 of the optical fibres are all provided on the same side of the flexible light-diffusing textile 2. The free sections 6 each bear one end 10 of the optical fibre. The free sections 6 of the optical fibres can be bundled and inserted into a brass ferrule 77 allowing optical connection to a light-emitting source 8. After gluing and cutting, the end of the optical fibres is highly polished such that an excellent surface is obtained. The ferrule 77 is used as a port of entry of light for an optical fibre connector 7 provided on the light-emitting source 8. The light-emitting source 8 is managed by a computerized control unit 9 and provides light according to set parameters to the light diffusing textile 2.

The flexible light-diffusing textile 2 of FIG. 1 can be provided with light only from one side. Additionally, free sections 6 of the optical fibres may be shorter than those of the embodiment of FIG. 1.

Free sections 6' of the optical fibres are also provided on the side opposite that of the light-emitting source 8. The free sections 6' each bear the other end 10' of the optical fibre. The flexible light-diffusing textile 2 is provided with two bundles of free (non woven) optical fibre free sections.

Accordingly, light may be provided at both ends of optical fibres. Hence, a ferrule 77', an optical connector 7', a light-emitting source 8', and a computerized unit 9' can be provided also on the other side of the flexible light-diffusing textile 2. Long free sections 6 allow using a single light-emitting source 8 connected to both ends 10, 10' of the flexible light-emitting source 2, rather than two light-emitting sources. Schematic FIG. 1 does not respect the real sizes since free sections 6, 6' could be longer for allowing connection to a single light-emitting source.

In the light-diffusing textile 2, the optical fibres 11 are woven with transverse yarns 14.

FIG. 2 shows a schematic example of an optical fibre woven with yarns 14. The optical fibre 11 has a core 12 and a thin cladding 13. In the example, it is bent around four yarns 14. In the example, light is propagated in the fibre from the right-hand side. Due to the bends, light will locally be incident on the core/cladding interface at an angle which exceeds a critical angle for that interface, whereby part of the light is allowed to locally escape from the core 12 of the fibre 11 according to the arrows. The cladding 13 is sufficiently diffusive to provide side diffusion of the light in direction of a treatment volume V. Most of the light is transmitted along the optical fibres, so that the light emitted in successive bends have similar features.

The example above is provided for a uniform weaving of optical fibres, and flat. However, one may search to optimize the lay-out of the fibres in order to promote the features of the emitted light, for example the uniformity of its features in the treatment volume, and to make it independent of the global radius of curvature of the textile.

So, according to one embodiment of the invention, the flexible light-diffusing textile is woven along a specific pattern in order to improve these features. One non-limiting example of such a pattern will be given below in relation to FIGS. 3 to 6.

Figure 4:
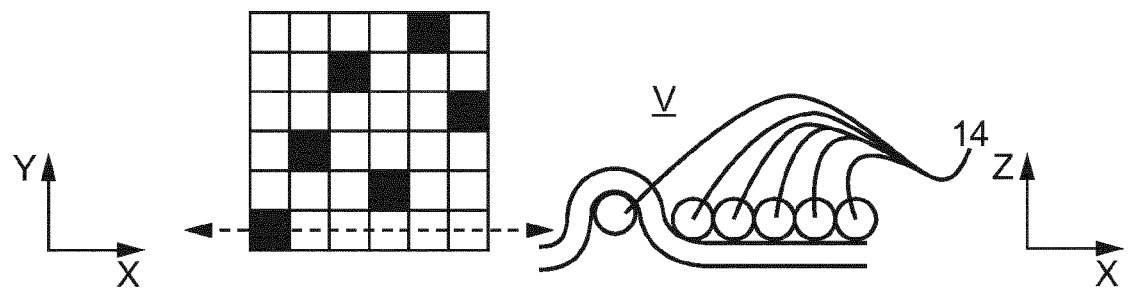
Figure 5:
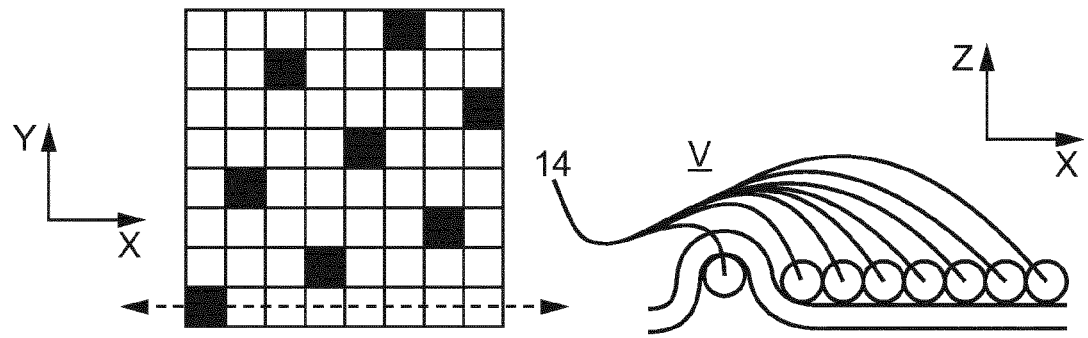

FIGS. 3-5 show, respectively, structures of satin weave 4, 6 and 8 patterns. "POF" means optical fibre. On each figure, the left-hand side crossboard is a top view of a pattern for this weave, and the right-hand side view is a cross-section along the arrow of the left-hand-side view. The weft threads represent the optical fibres 11, and the warp threads the transverse yarns 14.

So, light is intended to be propagated between the left side and the right side on each of these sketches. The black spot on the left-hand side crossboards shows that the weft thread is above the warp thread at that location. As can be understood from the right-hand side sketches, there are fewer places where the weft thread is above the warp thread, which in turns means that the bends above the warp threads are more severe (higher radius of curvature) than the bends below the warp threads, so that light will predominantly be propagated out of the core 12 above the warp threads toward the treatment volume V.

The lay-out of the satin weaves 4, 6 and 8 are self-explanatory from the drawings.

Figure 6:
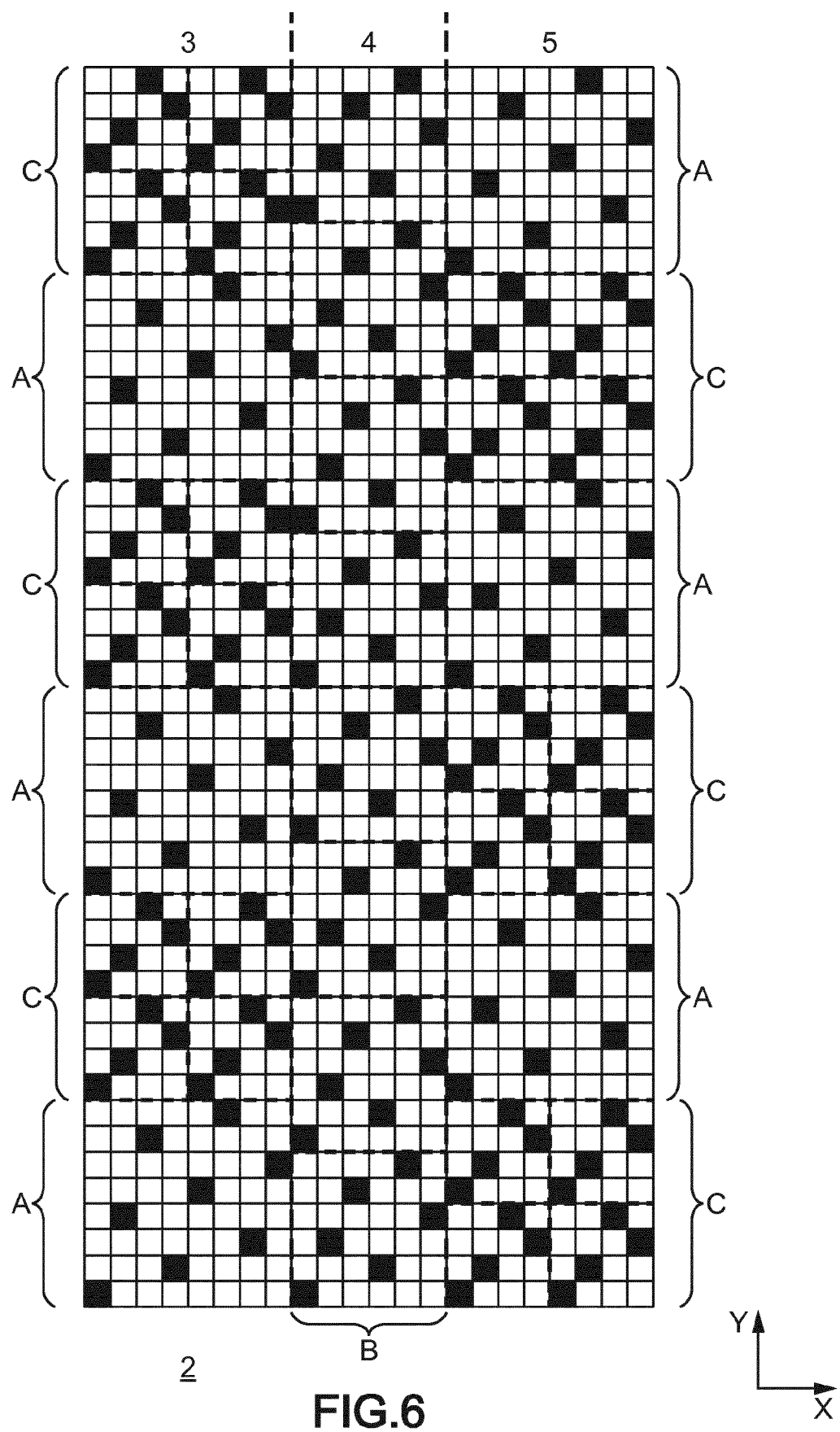
FIG. 6 is a top view of a woven pattern for the fabric of the medical device of FIG. 1.

FIG. 6 shows an example of a flexible light-diffusing textile 2 manufactured from threads woven according to the above patterns. As discussed above in relation to FIG. 1, the flexible light-diffusing textile 2 may comprise three consecutive portions 3, 4, 5. The portion 4 comprises, along the width, juxtaposed satin weave 6 panels such as the one described above in relation to FIG. 4. The portion 3 comprises an alternance of satin weave 4 panels and satin weave 8 panels such as described above in relation to FIGS. 3 and 5, respectively. Four satin weave 4 panels arranged in two rows and two columns provide a 8-thread pattern which can be alternated with a satin weave 8 panel. The portion 5 is complementary to portion 3. It is also provided as an alternance of one satin weave 8 panel and 4 satin weave 4 panels. A satin weave 8 panel is provided to correspond to satin weave 4 panels in the first portion 3.

This specific pattern is believed to provide a uniform illumination to the treatment volume V, regardless of the global flexibility of the light-diffuser textile.

Moving back to FIG. 1, according to this embodiment, from the left of the drawing, about 20 cm long free non-woven optical fibres are found, followed by a 21.5 cm long woven area comprising W1 weave (4.5 cm), W2 weave (3.0 cm), W3 weave (6.5 cm), W2 weave (3.0 cm) and W1 weave (4.5 cm) are then provided. On the opposite side, the free other ends of the optical fibres are found. Their length is also about 20 cm. The woven area is 5 cm wide and comprises 187 weft optical fibres (density 37 fibres per cm).

The free optical fibre portions are bundled and inserted into a connector 7 for connection to a light-emitting source 8.

All flexible light diffuser textiles can be woven using the hand weaving loom ARM B60 from Biglen (Switzerland).

The warp yarns will be described later.

Toray Raytela® PG series Polymethyl methacrylate optical fibres with fluorinated polymer cladding (refractive index 1.41) are introduced as weft using a modified shuttle. The fibre diameter thereof is 250 µm.

Weft density varies according to weave and is determined by optical count. The dimension of the flexible light diffuser textile manufactured is 21.5 cm (weft, named width, W)×15 cm (warp, named length, L). In order to connect the fabric to a light-emitting source, the total length of polymethyl methacrylate optical fibres is about 60 cm: 21.5 cm are woven and approximately 20 cm+20 cm on each side of the woven area are free. The density of the optical fibres is 37 per cm.

According to this example, the ferrule 77' of the flexible light-diffusing textile 2 was connected to a 635 nm LASER diode 8 (5 W, Dilas, Germany).

The LASER diode commercialised by DILAS (reference M1F4S22-638.3-5C-SS2.6) is used to illuminate the flexible light-diffusing textile. This LASER diode emits 5 Watt (W). It is equipped with a standard SMA connector 7 (ref DS11- lp-o8617-v0). The diode is mounted on a Peltier module (PE1-12707AC society Multicomp) to ensure the cooling of the diode.

The diode and the Peltier module are powered via a power supply OSTECH (ref DS11-lp-o8617). This power supply manages all functions of the diode and Peltier module, using a computer with a RS-232 connection. The control software is provided by OSTECH. It is therefore possible to manage the diode and Peltier module through a list of commands provided by OSTECH with a laptop at the convenience of the user.

The software allows to set the diode power (0 to 5 W), the time of illumination (1 s to 99 minutes), the delay of illumination (1 s to 99 minutes) and the number of illuminations (1-99).

The system further comprises a temperature-modifying system. The extension of the temperature-modifying system is similar to that of the light-diffusing textile. The temperature-modifying system is adapted to modify temperature in the whole treatment volume. According to the first embodiment above, the temperature-modifying system comprises the warp yarns 14. The warp yarns 14 comprise a phase-change material (or "PCM") which changes phase at a temperature in a temperature window at which temperature of the light-diffusing textile is to be regulated. For example, the temperature of the light-diffusing textile is to be regulated in a temperature window above body temperature, preferably slightly above body temperature, such as, for example, between 37° and 45° C., such that temperature in the treatment volume increases by at least 1° C., preferably by at least 5° C., and more preferably by 10° C. The temperature-increase remains limited and progressive for the comfort of the patient, and/or also not to harm the synthesized photosensitizer molecules. The warp yarns 14 comprise a material which changes phase at this temperature.

Because physical integrity of the warp yarn 14 is to be maintained even in case of a change of phase of the phase-change material to liquid or gaseous phase, the warp yarn 14 can be provided as a solid matrix 15 bearing or embedding individual capsules 16. The solid matrix 15 is made of a material which remains solid throughout the operating temperature range of the flexible light-diffusing textile. The capsule 16 comprises a solid shell 17 which surrounds an interior volume 18. The shell 17 remains solid throughout the operating temperature range of the flexible light-diffusing textile. The shell 17 is thin and resilient to adapt to any potential volume or shape change due to the phase change of the inner material. The shell 17 is made of a material which can be easily adhered to the matrix 15. A suitable material for the shell 17 is for example polystyrene. The interior volume comprises a phase change material which changes phase within the operating temperature range of the flexible light-diffusing textile. There are countless phase change materials, and it is inefficient to list them all here. One suitable class of phase-change material which can be used within the frame of the present embodiment is paraffin wax, for example Rubitherm paraffin RT42 or RT44HC.

As disclosed above, a suitable example for microcapsules 16 comprises paraffin wax encompassed in a rigid flexible shell. Styrene can be used as a suitable base material for the shell of these microcapsules.

Figure 7:
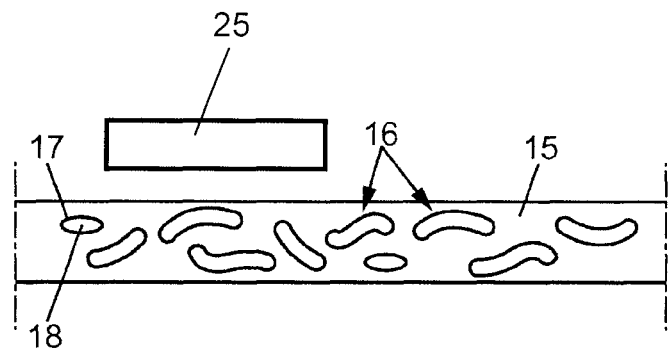
FIG. 7 is a partial view of a warp yarn for the embodiment of FIG. 1.

A suitable example of material for the matrix 15 of the warp yarn 14 is polyester. According to an embodiment, as shown on FIG. 7, the warp yarn 14 comprises a matrix 15 of polyester bearing capsules 16 encompassing paraffin wax.

The microcapsules can be applied to the matrix by numerous techniques, including stamping, dyeing, impregnation, spraying and coating or by direct incorporation in the matrix. If necessary, suitable binders can be used to promote the adherence of the capsules to the yarn. For example, polymeric binders can be used.

Figure 8:
FIG. 8 is a microscopy photograph of the surface of the yarn of FIG. 7.

FIG. 8 shows an example of a photograph of PRS® paraffin wax-containing capsules to be bound to the matrix 15 of the warp yarn 14.

Figure 9:
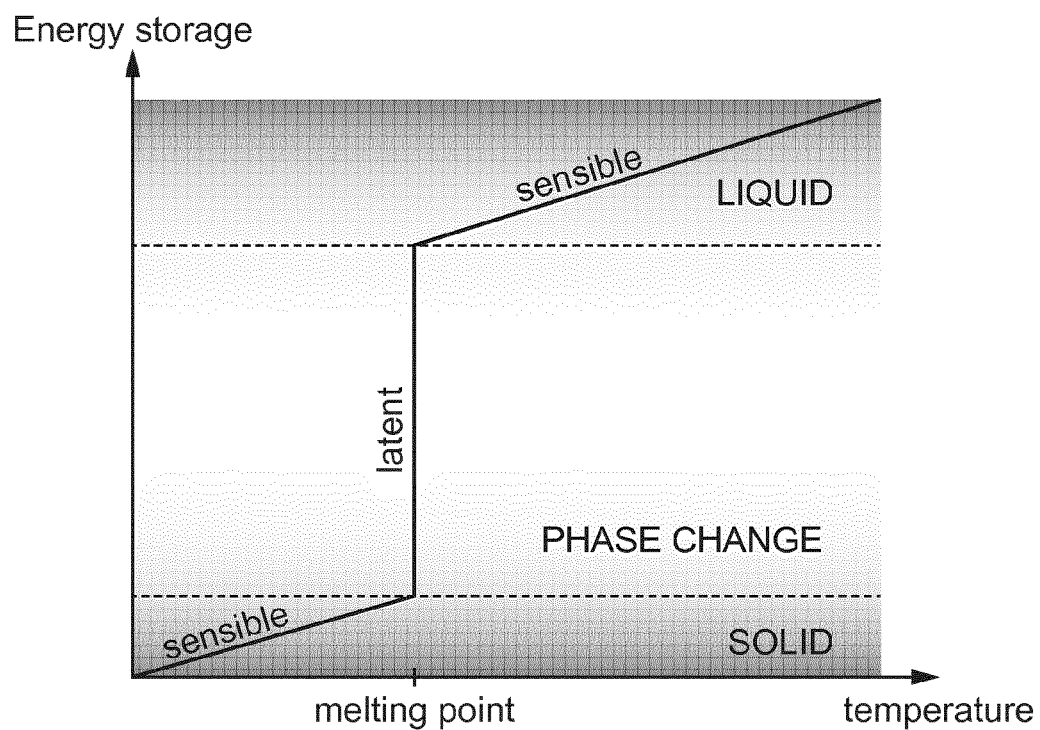
FIG. 9 is a diagram of energy vs temperature illustrating the phase change phenomenon.

FIG. 9 is a schematic graph of energy storage vs temperature for a phase change material. As can be understood, during the phase change from the liquid state (top) to the solid state (bottom), energy is released from the phase change material without a temperature change. Providing a device at a controlled temperature during a given time in the vicinity of the treatment volume will enable to modify the temperature within the treatment volume during this time.

The light diffusing textile is functionalised with materials able to keep skin surface temperature close to 42° C. during a minimum time of 30 minutes. Different possibilities exist. Among these one, PCM (Phase Change Materials) including paraffin is suitable for this application. These materials are interesting as they can store heat avoiding to use any energy source when the patient uses the device. Consequently, no electrical connection will be required during the PDT procedure. This ambulatory system ensures a maximum efficiency of the PDT treatment.

PCMs absorb or release thermal energy to limiting heat transfer to a sudden temperature change. By a change of liquid-solid phase of the material, it produces a thermal storage of heat when they are in the liquid state and can restitute energy becoming in the solid state in the proximity of their melting temperature. This energy storage is increased with a higher fusion enthalpy. Among PCMs which can be used with the present textile, some organic PCMs present one or more of the following advantages for the project:

not corrosive;
chemically and thermally stable;
No or little subcooling.

As applied on a fabric for breathability and comfort of the wearer, the great advantage of microencapsulated PCMs is their exchange surface with their environment, which gives them a maximum efficiency.

Microencapsulated PCMs already have shown their efficiency for heat exchanger-system and presents a possibility for stabilisation of temperature during a long period (Heinz, A., Streicher, W., 2006. Application of Phase Change Materials and PCM slurries for thermal energy storage, Ecostock Conference, 31 May-2 Jun. 2006, Pomona, USA).

The device which has just been described can be operated as follows.

Before operation, the system 1 can be stored in a regulated temperature environment, where its temperature is maintained above the phase-change temperature. For example, the system 1 is stored in a heater 25 at a temperature of about 42° C. Preferably, it is held at a temperature which is bearable by the human skin.

A suitable precursor can be applied to the patient. For example, a precursor is topically applied in areas to be treated.

When it is to be used, the flexible light-diffusing textile 2 is wrapped around the treatment volume. No light is emitted yet. Because the ambient air is of lower temperature than that of the flexible light-diffusing textile, the flexible light-diffusing textile begins to cool down. During this step, it warms up the treatment volume. The flexible light-diffusing textile cools down until it reaches the phase change temperature of the phase change material (this step can be rather short if the heater maintains temperature of the phase change material just above the phase change temperature). During a given amount of time, the temperature of the treatment volume will be raised by the fact that the temperature of the phase change material remains constant above the initial temperature of the treatment volume, as the phase change material emits/absorbs energy to change phase.

Due to the temperature increase, more photosensitizer will be synthesized in areas to be treated. In addition, the present embodiment using phase-change materials, enables to generate a uniform and controlled field of temperature in the treatment volume, which in turn enables a uniform efficiency in synthesis of the photosensitizer.

That step can for example be performed for a duration of the order of minutes, for example about 10 minutes to one hour, during for example 25-45 minutes. During that time, during which the photosensitizer achieves efficient synthesis, the patient needs not remain in the waiting room in the hospital, s/he could run errands.

After synthesis has been achieved, photodynamic therapy can be performed. Photodynamic therapy can include emission of treatment light (red light) and, optionally of inhibiting light (blue light). The light-emitting source 8 is designed accordingly, and the control unit 9 is operated accordingly to emit the needed light at the needed moment according to one of pre-set protocols. At that time, the light-emitting source 8 can be made to emit light under a light-emission pattern controlled by the control unit 9. If the control unit 9 and the light-emitting source 8 can be operated from a battery, the patient needs not to remain in the waiting room in the hospital either during that time. Any suitable protocol for emitting light can be performed with the present device, such as emitting continued or pulsed light, emitting light of one or more frequencies simultaneously or in sequence, as is known in the art. Advantageously, since the temperature-modifying system and the photodynamic-therapy device are integrated together, there is scarcer need for any intermediate intervention by a practitioner between the photosensitizer-synthesis mode and the therapeutic mode.

The system could comprise a clock which can be programmed to initiate the emission of light after a given time. The time can be predetermined as a time thought to be sufficient for sufficient photosensitizer to be synthetized. The time could be patient-specific. Hence, the system can comprise a user interface adapted to set a time into the system.

Above, a case has been disclosed where the whole system 1 is kept in the heater before use. However, the flexible light-diffusing textile 2 only could be maintained in the heater, and plugged to the light-emitting source 8 after applying the flexible light-diffusing textile 2 to the patient, or just before starting the illumination sequence.

The example above includes two light-emitting sources 8, 8'. However, in a variant embodiment, the system may comprise a single light-emitting source 8. This embodiment is schematically illustrated on FIG. 10. According to this embodiment, the second end 10' of the optical fibres could be connected to an optical detector 19 such as a CCD.

Since the efficiency of photodynamic therapy (PDT) depends on the amount of singlet oxygen which itself depends on the amount of synthesized photosensitizer because, for a photodynamic reaction to occur, the photosensitising agent, activating light and oxygen must be present in sufficient amounts, it is important to determine the amount of active photosensitising agent remaining at the site of action. In fact degradation of the photosensitiser occurs during treatment and this effect is named photobleaching.

The measurement of photobleaching allows knowing the efficacy of photodynamic therapy and adjusting the light treatment. The principle of measurement is to estimate the amount of singlet oxygen produced by photodynamic therapy by measuring the rate of photobleaching of the photosensitizer by measuring the fluorescence. For example for protoporphyrin IX, an excitation light at 405 nm and collecting the fluorescence at 630 nm can be used.

Figure 10:
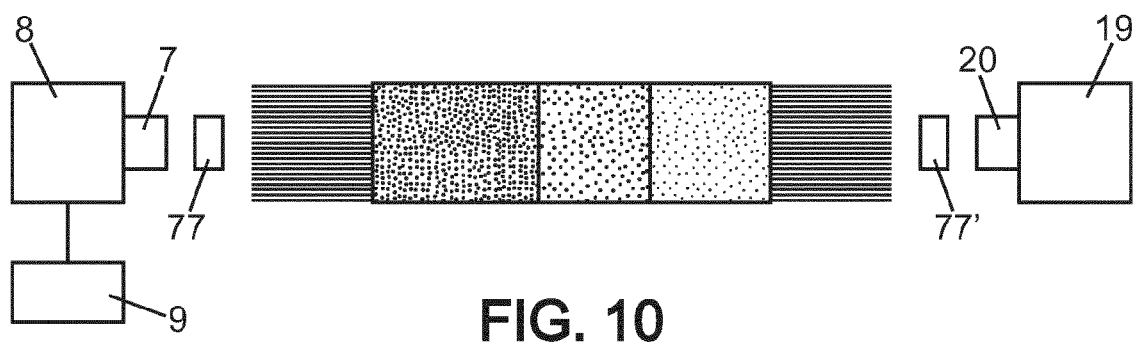
FIG. 10 is a view similar to FIG. 1 for a second embodiment.

FIG. 10 schematizes an embodiment of a medical device comprising a flexible light-diffusing textile comprising one bundle of optical fibres for therapy and one bundle of optical fibres for detection of bleaching. The left-hand side bundle collects optical fibres specifically used for therapy and the right-hand side bundle collects optical fibres specifically used for detection of bleaching. The latter fibres are bundled into a highly polished brass ferrule 77' allowing optical connection to the photodetector 19 through an optical connector 7'. The light-emitting source 8 may provide two different wavelengths, one for therapy and one adapted to improve the accuracy of the detector to detect light produced by a photosensitizer substance. Indeed, when it is activated by light, the photosensitizer fluoresces, and part of this light may enter the optical fibres and propagate within the fibres up to the detector 19. The control unit 9 is therefore connected to the detector 19 and is designed to discriminate the light emitted by the light-emitting source 8 from the light fluorescing from the photosensitizer. As the amount of detected fluorescent light decreases, the control unit can determine that photosensitizer does not fluoresce any more, and this would be because the photosensitizer has been consumed, and hence the treatment is finished.

Although, in the above embodiment, all optical fibers can be used to both transmit emitted light toward the treatment volume and transmit fluorescence light toward the detector, some light fibers could be dedicated to photodynamic therapy and some to detection. For example, the photodynamic therapy light fibres could be connected to one photodynamic therapy light-emitting source at one end, and not connected at the other end, whereas the other fibers would be connected to the reading-improving light-source at one end and to the detector at the other end. This could be easily achieved by gaining advantage of the long non-woven portions 6 of the optical fibres to group light fibres to respective light-emitting sources, even if at the treatment volume, the fibres of the two groups are alternated. Yet, the number of detection fibres should remain low so as not to reduce therapeutic light emission homogeneity.

According to yet another embodiment, the medical device 1 has a structure as shown in FIG. 1. However, the light-emitting source can be controlled to emit infra-red light at a controlled frequency, in addition to light suitable for photodynamic therapy. In this embodiment, the temperature-modifying system comprises the light-emitting source 8 (or sources 8, 8') set to emit light at an infra-red frequency, and the optical fibres 11 transmitting and emitting this light toward the treatment volume. According to this embodiment, the light-emitting source 8 must be coupled to the light fibers already during the temperature regulation stage of operation of the medical device. In this embodiment, the transverse warp yarns could be similar to the first embodiment above, for an additional temperature-modifying effect provided by both the phase-change material and the infra-red light, or they could be of a material which does not change phase at the operating temperatures, such as plain polyester. In operation, the light source could be set first in infra-red light emission mode in order to address infra-red light according to pre-set parameters toward the treatment volume, ensuring a temperature-modifying in a desired temperature range, until synthesis of the photosensitizer is achieved. Then, the light source is set in photo-dynamic therapy mode. In that case, the same fibres are used for both modes. Alternatively, some fibres could be dedicated to infra-red light and some other to photo-dynamic therapy light by connecting alternately the end of some fibres to alternative light sources.

In such an embodiment, the system may include a temperature-regulation system 30. One or more thermo sensors 31 can be attached to the light diffusing textile and connected to a controller 32. The thermo-sensors 31 are designed to sense temperature. Such sensors 31 are currently commonly available, which are compatible with the above embodiment. The controller 32 is designed to compare the sensed temperature with a target temperature, and to control the light-emitting source as a result of this comparison. Control of the light-emitting source can be periodic, and can include starting, maintaining, stopping the light-emitting source, or controlling a parameter of the light-emitting source, such as the spectrum of the emitted-light or the number or density of light-fibers addressed by the light-emitting source.

Figure 11:
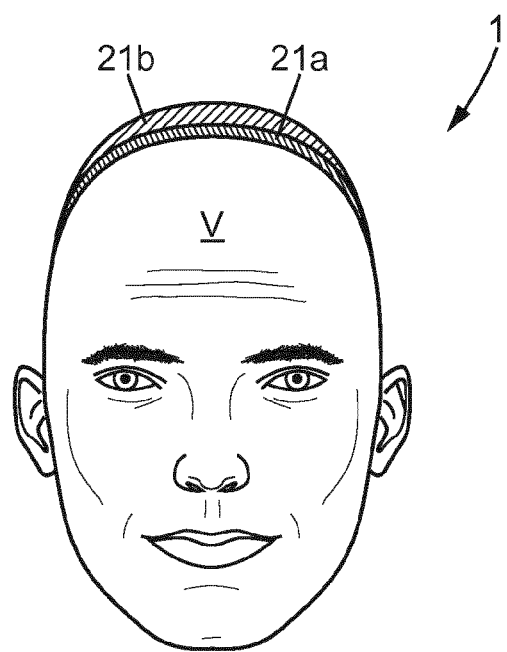
FIG. 11 is a schematic view of using the medical device according to a third embodiment.

According to yet another embodiment, as shown on FIG. 11, the system 1 may comprise a plurality of layers 21a, 21b. The first layer 21a could be a flexible light-diffusing textile 2 such as described in any of the above embodiments. The second layer 21b could be a thermo-modifying layer. Preferably, the first layer 21a is provided between the treatment volume and the second layer 21b. The thermo-modifying layer can be flexible, with a flexibility similar to that of the first layer 21a. It could be set to any given temperature in a pre-determined temperature range. For example, the second layer 21b would comprise a textile comprising electrically-insulating wires and an electrical wire connected to a power source, and acting as an electrical resistance which is heated by passage of an electrical current. The power delivered by the power source can be tailored according to the monitored temperature in the treatment volume.

As explained above, this embodiment could be combined with one or more of the above embodiments. However, in variant, the second layer 21b could be combined with a flexible light-diffusing textile 2 as first layer 21a having no thermo-regulation ability.

As will be understood from the above description, the flexible light-diffusing textile can be wrapped around a treatment volume of the patient in a position where it has a concave shape surrounding a portion of the patient. For example, the flexible light-diffusing textile could be provided as a mask.

The above described method and device could also be used for the treatment of Hidradenitis suppurativa.

Although, in the above embodiments, temperature modification is performed before the photo-dynamic therapy treatment, there are variant uses where it could be performed simultaneously to the photo-dynamic therapy treatment. The above described systems could be applied. One example is the case of treatment of deep tumors. The above embodiments can achieve the following temperature field in the treatment volume: the temperature at a depth of 2 mm from the surface reaches 43° C., at a depth of 4 mm, the temperature reaches 39.5° C., while at a depth of 6 mm the temperature stays around 37.0° C. The antitumor effect of photodynamic therapy with ALA hexyl ester in a squamous cell carcinoma tumor could be improved with the above temperature field.

According to one example, using conventional PCM microcapsules, for the heating of a entire scalp (surface: 660 cm$^2$), 230 grams of PCM microcapsules (for example Rubitherm® RT42) are required to maintain the temperature of the light-diffusing textile at 42° C. for 30 minutes.

The invention claimed is:

1. A system comprising:
    a bundle of light fibers, each light fiber comprising at least one connection end to be connected to a light-emitting source, and a longitudinal body adapted both to transmit light inside the light fiber along the longitudinal body and to emit light outside the longitudinal body along the longitudinal body toward a treatment volume,
    a temperature-modifying system attached to the bundle of light fibers and adapted to modify temperature in the treatment volume by at least 1° C.,
    wherein the temperature-modifying system comprises a phase-change material adapted to change phase within a pre-set temperature range between 37° C. and 45° C.,
    wherein the system further comprises a heater adapted to pre-heat the phase change material at a temperature within the pre-set temperature range so as to increase temperature in the treatment volume by at least 1° C., and
    wherein the temperature-modifying system comprises yarns extending transverse to the light fibers, the phase-change material being integral with said yarns.

2. System according to claim 1, wherein the bundle of light fibers is encompassed within a first layer, and the temperature-modifying system is provided as a second layer, superimposed with the first layer.

3. System according to claim 1, wherein the bundle of light fibers comprises a light-emitting end and an opposite connection end, and wherein the temperature-modifying system comprises an infra-red light-emitting source connected to said connection ends of the light fibers of the bundle, and a control system adapted to have the infra-red light-emitting source emit infra-red light to modify temperature in the treatment volume.

4. System according to claim 1, wherein said yarns and said light fibers are woven together.

5. System according to claim 1, wherein the bundle of light fibers has a concave shape adapted to wrap around a convex part of a human body.

6. System according to claim 1, wherein the bundle of light fibers is flexible.

7. System according to claim 1, comprising a temperature-regulation system, wherein the temperature-regulation system comprises a sensor attached to the bundle of light fibers, and adapted to detect temperature in the treatment volume, a controller adapted to receive temperature information from the sensor and to control the temperature-modifying system according to the temperature information.

8. System according to claim 1, further comprising a light-emitting source optically connected to the connection ends, and adapted to emit light into the light fibers.

9. System according to claim 8, wherein the light-emitting source is settable to emit light at one or more pre-set wavelength range used in photodynamic therapy.

10. System according to claim 8, further comprising an optical detector which detects fluorescence light entering at least one of the light fibers from the treatment volume.

* * * * *